United States Patent
Harada et al.

(10) Patent No.: US 8,421,449 B2
(45) Date of Patent: Apr. 16, 2013

(54) EDDY-CURRENT FLAW DETECTION METHOD, EDDY-CURRENT FLAW DETECTION DEVICE AND EDDY-CURRENT FLAW DETECTION PROBE

(75) Inventors: Yutaka Harada, Osaka (JP); Junri Shimone, Osaka (JP); Kotaro Maeda, Osaka (JP)

(73) Assignee: Nuclear Engineering, Ltd., Osaka-Shi (JP)

( * ) Notice: Subject to any disclaimer, the term of this patent is extended or adjusted under 35 U.S.C. 154(b) by 421 days.

(21) Appl. No.: 12/679,222

(22) PCT Filed: Aug. 29, 2008

(86) PCT No.: PCT/JP2008/065504
§ 371 (c)(1),
(2), (4) Date: Mar. 19, 2010

(87) PCT Pub. No.: WO2009/037954
PCT Pub. Date: Mar. 26, 2009

(65) Prior Publication Data
US 2010/0231210 A1    Sep. 16, 2010

(30) Foreign Application Priority Data
Sep. 20, 2007    (JP) .................................. 2007-244461

(51) Int. Cl.
*G01N 27/82* (2006.01)

(52) U.S. Cl.
USPC ........................................................ 324/240

(58) Field of Classification Search .......................... None
See application file for complete search history.

(56) References Cited

U.S. PATENT DOCUMENTS

| 6,310,476 B1 * | 10/2001 | Kawanami et al. ........... 324/241 |
| 6,339,327 B1 | 1/2002 | Potiquet et al. |
| 2002/0130659 A1 * | 9/2002 | Wincheski et al. ........... 324/235 |

FOREIGN PATENT DOCUMENTS

| JP | 06-160357 | 6/1994 |
| JP | 08-334498 | 12/1996 |
| JP | 2000-235018 | 8/2000 |
| JP | 2000-235019 | 8/2000 |
| JP | 2000-235020 | 8/2000 |
| JP | 2001-509259 | 7/2001 |
| JP | 2003-344360 | 12/2003 |
| JP | 2006-010438 A | 1/2006 |
| JP | 2006-226884 | 8/2006 |

* cited by examiner

*Primary Examiner* — Jermele M Hollington
(74) *Attorney, Agent, or Firm* — Muncy, Geissler, Olds & Lowe, PLLC (57) ABSTRACT

An eddy-current flaw detection device comprises a magnetic element group of which a specified number of magnetic elements are evenly spaced in each of at least two rows around the surface of a column shaped casing that can be inserted into a conductive pipe, with one row being located at a different position from the other row by ½ the even spacing in the row direction, and switching circuits for switching the magnetic elements in the respective row at time-division. The elements of one row function as magnetic field excitation elements, the elements of the other row function as magnetic field detection elements, and the eddy-current flaw detection device performs eddy-current flaw detection of the conductive pipe by detecting magnetic field excited by magnetic field excitation element by two magnetic field detection elements located at different positions from the magnetic field excitation elements by 3/2 the even spacing.

20 Claims, 6 Drawing Sheets

FIG. 3A
RELATED ART
FIRST TIMESLOT

FIG. 3B
RELATED ART
SECOND TIMESLOT

FIG. 3C
RELATED ART
FIFTEENTH TIMESLOT

FIG. 3D
RELATED ART
SIXTEENTH TIMESLOT

FIG. 6A FIRST TIMESLOT

FIG. 6B SECOND TIMESLOT

FIG. 6C SEVENTH TIMESLOT

FIG. 6D EIGHTH TIMESLOT

EDDY-CURRENT FLAW DETECTION METHOD, EDDY-CURRENT FLAW DETECTION DEVICE AND EDDY-CURRENT FLAW DETECTION PROBE

This application is the normal phase under 35 U.S.C. §371 of PCT International Application No. PCT/JP2008/065504 which has an International filing data of Aug. 29, 2008 and designated the United States of America.

BACKGROUND

1. Technical Field

The present invention relates to improvements of an eddy-current flaw detection method, eddy-current flaw detection device and eddy-current flaw detection probe that are used in nondestructive inspection (eddy-current flaw detection testing) of a heat transfer pipe inside of a heat exchanger.

2. Description of Related Art

Figure 1:
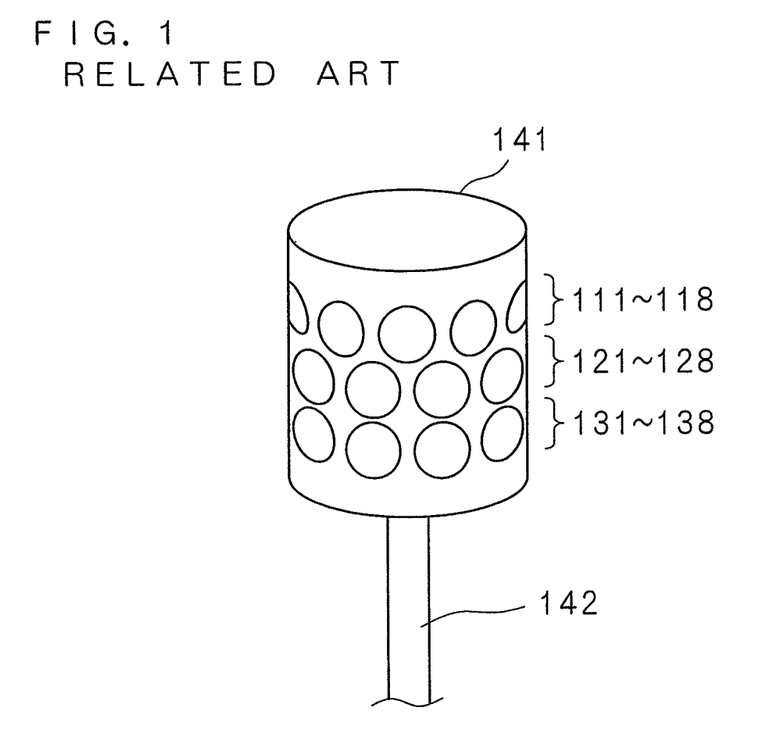
FIG. 1 is a perspective drawing schematically illustrating the external appearance of a conventional eddy-current flaw detection probe.

FIG. 1 is a perspective drawing schematically illustrating the external appearance of a conventional eddy-current flaw detection probe that is used in an eddy-current flaw detection device for a slim metal pipe, which is a heat transfer pipe (conductive pipe) inside of a heat exchanger.

Eddy-current flaw detection testing is a nondestructive inspection that applies a magnetic field that changes over time (AC current or the like) to a conductor, and detects when an eddy current, which occurs in the conductor, changes due to flaws; and in eddy-current flaw detection testing of a slim metal pipe, detection is performed while moving an eddy-current flaw detection probe that has been gently inserted inside the slim metal pipe.

This eddy-current flaw detection probe comprises a column-shaped casing (housing) 141 that is formed such that it can be gently inserted inside a slim metal pipe, and eight coils 111 to 118, 121 to 128, 131 to 138, that are aligned around the outer surface of the casing 141, are evenly spaced in each of three rows. The coils 111 to 118 of the first row of the three rows are arranged such that they are located at a position in the circumferential direction that differs from that of the coils 121 to 128 and 131 to 138 of the other two rows by ½ the equal spacing between coils.

Figure 2:
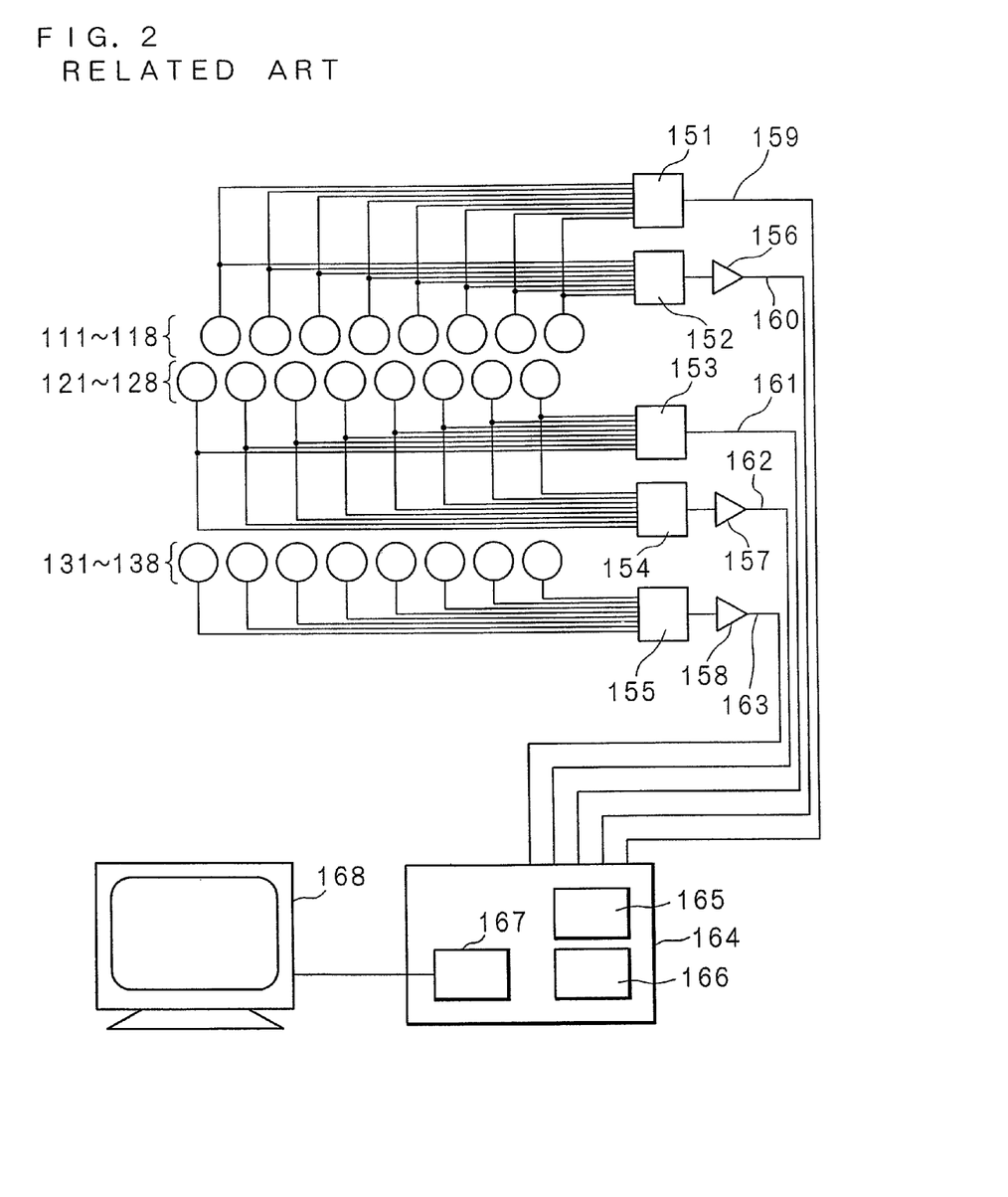
FIG. 2 is a block diagram illustrating the circuit construction inside the casing of a conventional eddy-current flaw detection probe and eddy-current flaw detection device.
Figure 3A:
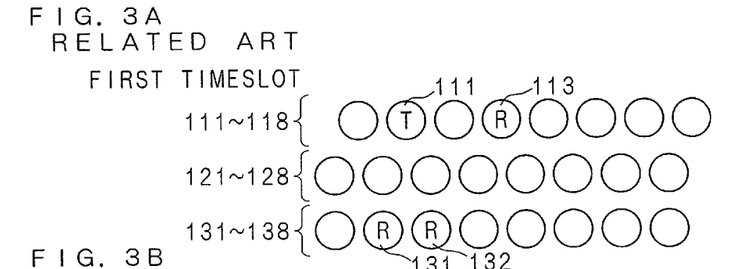
FIG. 3A is an expanded view explaining the operation of a conventional eddy-current flaw detection probe during a first timeslot, and illustrating a planar expansion of the coils shown in FIG. 1.
Figure 3B:
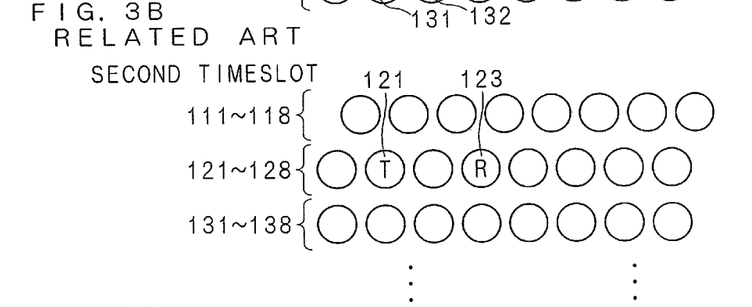
FIG. 3B is an expanded view explaining the operation of a conventional eddy-current flaw detection probe during a second timeslot, and illustrating a planar expansion of the coils shown in FIG. 1.
Figure 3C:
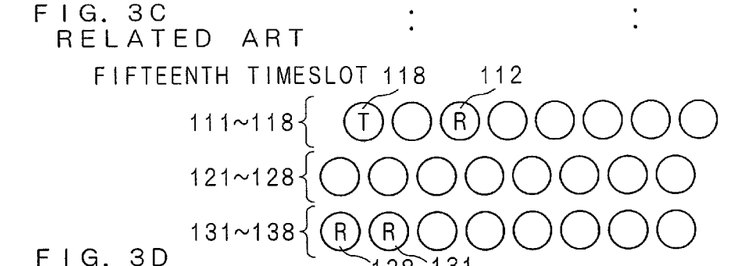
FIG. 3C is an expanded view explaining the operation of a conventional eddy-current flaw detection probe during a fifteenth timeslot, and illustrating a planar expansion of the coils shown in FIG. 1.
Figure 3D:
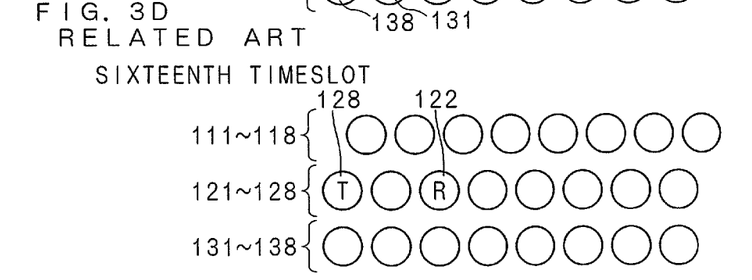
FIG. 3D is an expanded view explaining the operation of a conventional eddy-current flaw detection probe during a sixteenth timeslot, and illustrating a planar expansion of the coils shown in FIG. 1.

FIG. 2 is a block diagram illustrating the circuit construction inside the casing 141 and eddy-current flaw detection device.

The coils 111 to 118 in the first row are coils that are jointly used as magnetic field excitation coils and magnetic field detection coils, and each of these is connected to a multiplexer (switching circuit) 151 for magnetic field excitation, and to a multiplexer (switching circuit) 152 for magnetic field detection.

A lead wire 159 is connected to the multiplexer 151 for magnetic field excitation, and an AC current for exciting a magnetic field is applied to the lead wire 159 from the main unit 164 of the eddy-current flaw detection device. An amplifier 156, which amplifies the output signal of the magnetic field that is detected by the coils 111 to 118, is connected to the multiplexer 152 for magnetic field detection, and the signal that is amplified by the amplifier 156 is outputted to the main unit 164 of the eddy-current flaw detection device via a lead wire 160.

Moreover, the coils 121 to 128 in the second row are also coils that are jointly used as magnetic field excitation coils and magnetic field detection coils, and each of these coils is connected to a multiplexer (switching circuit) 153 for magnetic field excitation, and to a multiplexer (switching circuit) 154 for magnetic field detection.

A lead wire 161 is connected to the multiplexer 153 for magnetic field excitation, and an AC current for exciting a magnetic field is applied to the lead wire 161 from the main unit 164 of the eddy-current flaw detection device. An amplifier 157, which amplifies the output signal of the magnetic field that is detected by the coils 121 to 128, is connected to the multiplexer 154 for magnetic field detection, and the signal that is amplified by the amplifier 157 is outputted to the main unit 164 of the eddy-current flaw detection device via a lead wire 162.

The coils 131 to 138 in the third row are magnetic field detection coils, and each of these is connected to a multiplexer (switching circuit) 155 for magnetic field detection.

An amplifier 158, which amplifies the output signal of the magnetic field that is detected by the coils 131 to 138, is connected to the multiplexer 155 for magnetic field detection, and the signal that is amplified by the amplifier 158 is outputted to the main unit 164 of the eddy-current flaw detection device via a lead wire 163.

As shown in FIG. 1, the lead wires 159 to 163 are stored inside a cable 142 that connects the center section of the surface on one end of the casing 141 of the eddy-current flaw detection probe with the main unit 164 of the eddy-current flaw detection device.

An oscillation circuit 165 that produces an AC current for exciting a magnetic field by coils 111 to 118 and 121 to 128, a signal detection circuit 166 that obtains amplified detection signals of magnetic fields that are detected by coils 111 to 118, 121 to 128 and 131 to 138, and a communication unit 167 for communicating with a personal computer (or workstation) 168 are stored inside of the main unit 164 of the eddy-current flaw detection device. The personal computer 168 receives the detection signal that was obtained by the signal detection circuit 166 via the communication unit 167 as detection data, and records and displays the received detection data.

FIGS. 3A to 3D are expanded views explaining the operation of an eddy-current flaw detection probe having this kind of construction, and illustrating a planar expansion of the coils 111 to 118, 121 to 128 and 131 to 138 shown in FIG. 1.

According to such eddy-current flaw detection probe, in a first timeslot representing operation cycle (FIG. 3A), the multiplexer 151 selects coil 111 as the magnetic field excitation coil T, and multiplexer 152 selects coil 113, which is located at a position that differs two coils amount ahead of coil 111 in the circumferential direction of selection, as the magnetic field detection coil R. In addition, multiplexer 155 selects coils 131 and 132 in the third row, which are separated from coil 111 by an amount of 0.5 coil in the circumferential direction, as magnetic field detection coils R.

According to the eddy-current flaw detection probe, in a second timeslot (FIG. 3B), the multiplexer 153 selects coil 121 in the second row, which is located at a position that differs 0.5 coil amount behind coil 111 in the circumferential direction of selection, as the magnetic field excitation coil T, and the multiplexer 154 selects coil 123, which is located at a position that differs two coils amount ahead of coil 121 in the circumferential direction of selection, as the magnetic field detection coil R.

After that, in odd number timeslots, the multiplexer 151 sequentially selects coils 112, 113, 114, . . . as the magnetic field excitation coil T, and the multiplexer 152 sequentially selects coils 114, 115, 116, . . . as the magnetic field detection coil R. Moreover, the multiplexer 155 sequentially selects two coils 132•133, 133•134, 134•135, . . . as magnetic field detection coils R.

In even number timeslots, the multiplexer 153 sequentially selects coils 122, 123, 124, . . . as the magnetic field excitation coil T, and the multiplexer 154 sequentially selects coils 124, 125, 126 as the magnetic field detection coil R.

According to the eddy-current flaw detection probe, in a fifteenth timeslot (FIG. 3C), the multiplexer 151 selects coil 118 as the magnetic field excitation coil T, and the multiplexer 152 selects coil 112, which is located at a position that differs two coils amount ahead of coil 118 in the circumferential direction of selection, as the magnetic field detection coil R. In addition, the multiplexer 155 selects coils 138, 131 in the third row, which are separated from coil 118 by an amount of 0.5 coil in the circumferential direction, as magnetic field detection coils R.

According to the eddy-current flaw detection probe, in a sixteenth timeslot (FIG. 3D), the multiplexer 153 selects coil 128 in the second row, which is located at a position that differs 0.5 coil amount behind coil 118 in the circumferential direction of selection, as the magnetic field excitation coil T, and the multiplexer 154 selects coil 122, which is located at a position that differs two coils amount ahead of coil 128 in the circumferential direction of selection, as the magnetic field detection coil R.

From the above, this flaw detection probe can obtain, for each circumference around a slim metal pipe, eight channels of output from coils 111 to 118 for detecting flaws in the circumferential direction, eight channels of output from coils 121 to 128 for detecting flaws in the circumferential direction, and 16 channels of output from coils 131 to 138 for detecting flaws in the axial direction. The output signals from coils 111 to 118 and the output signals from coils 121 to 128 are in a positional relationship that interpolate between each other in the circumferential direction, so the output for detecting flaws in the circumferential direction becomes a total of 16 channels.

Japanese Patent Application Laid-Open No. 2000-235018 discloses an eddy-current flaw detection probe that comprises a plurality of excitation coils, a plurality of detection coils, and a switching circuit for time-division driving of these coils, and that further comprises an insulation switching circuit between the coils and switching circuit.

Japanese Patent Application Laid-Open No. 2000-235019 discloses an eddy-current flaw detection probe that comprises a plurality of magnet field excitation elements, a plurality of magnetic field detection elements, a switching circuit for time-division driving of these elements, and a detection signal amplification circuit that is provided further on the measurement instrument side than the switching circuit that time-division drives the plurality of magnetic field detection elements.

Japanese Patent Application Laid-Open No. 2000-235020 discloses an eddy-current flaw detection device that comprises an eddy-current flaw detection probe having a plurality of magnetic field excitation elements and magnetic field detection element pairs, and means for time-division driving of the magnetic field excitation elements and magnetic field detection element pairs of that probe, and further comprises a control device that includes means for keeping output signals from each element pair over a number of time-division driving steps, and means for finding the difference between the output signals from adjacent element pairs.

SUMMARY

In the conventional eddy-current flaw detection probe described above, there is a positional shift in the axial direction between the output of the 8 channels from coils 111 to 118 and the output of the 8 channels from coils 121 to 128 for detecting flaws in the circumferential direction, and when there is fluctuation in the scanning speed of the eddy-current flaw detection probe, it is difficult to compensate for that positional shift in the axial direction. When it is not possible to compensate for the positional shift in the axial direction, there are problems that the spatial resolution of the flaw detection signals drops, as well as the signal reproducibility during redetection of flaws drops.

Moreover, in the eddy-current flaw detection probe described above, coils 111 to 118 and 121 to 128 are jointly used as magnetic field excitation coils and magnetic field detection coils, and are connected to both a switching circuit for magnetic field excitation and a switching circuit for magnetic field detection, so there are problems that circuit construction becomes complicated, and interference signals due to crosstalk occur.

The present invention has been made with the aim of solving the above problems, and it is an object of first to third aspects of the invention to provide an eddy-current flaw detection method that improves the spatial resolution of flaw detection signals and the signal reproducibility during redetection of flaws, and reduces signal interference due to crosstalk with a simple circuit construction.

The object of fourth to ninth aspects of the invention is to provide an eddy-current flaw detection device that improves the spatial resolution of flaw detection signals and the signal reproducibility during redetection of flaws, and reduces signal interference due to crosstalk with a simple circuit construction.

The object of tenth to fifteenth aspects of the invention is to provide an eddy-current flaw detection probe that improves the spatial resolution of flaw detection signals and the signal reproducibility during redetection of flaws, and reduces signal interference due to crosstalk with a simple circuit construction.

The eddy-current flaw detection method according to a first aspect of the invention is an eddy-current flaw detection method for performing eddy-current flaw detection of a conductive pipe by using a magnetic element group of which a specified number of elements are evenly spaced in each of at least two rows that are formed around the surface of a column shaped casing that is formed such that it can be inserted into the conductive pipe, with one of the two rows being located at a position that differs from the other row by ½ the even spacing in the row direction, and switching circuits for switching the magnetic elements in the respective row of the magnetic element group at time-division; and is characterized by comprising: a step of causing the switching circuit to switch magnetic elements in one row at time-division in order to excite a magnetic field; and a step of causing the switching circuit to switch, at time-division, two of the magnetic elements that are arranged in the other row and that are located at positions that differ from the magnetic element that excited the magnetic field by 3/2 the even spacing in the row direction in order to detect the excited magnetic field.

The eddy-current flaw detection method according to a second aspect of the invention is an eddy-current flaw detection method for performing eddy-current flaw detection of a conductive pipe by using a magnetic element group of which a specified number of elements are evenly spaced in each of at least two rows that are formed around the surface of a column shaped casing that is formed such that it can be inserted into the conductive pipe, with one of the two rows being located at a position that differs from the other row by ½ the even spacing in the row direction, and switching circuits for switching the magnetic elements in the respective row of the magnetic element group at time-division; and is characterized by comprising: a step of preparing the magnetic elements in one row as magnetic field excitation elements that excite a magnetic field, and the magnetic elements in the other row as magnetic field detection elements that detect a magnetic field; a step of causing the switching circuit to switch magnetic field excitation elements at time-division in order to excite a magnetic field; and a step of causing the switching circuit to switch, at time-division, two of the magnetic field detection elements that are arranged in the other row and that are located at positions that differ from the magnetic field excitation element that excited the magnetic field by 3/2 the even spacing in the row direction in order to detect the excited magnetic field.

The eddy-current flaw detection method according to a third aspect of the invention is characterized by comprising: a step of preparing a magnetic element group that is located in a row around the surface of the casing adjacent to the other row, and a switching circuit for switching the magnetic element group at time-division; and a step of causing the switching circuit to switch, at time-division, two magnetic elements that are located in the row in order to detect the excited magnetic field.

The eddy-current flaw detection device according to a fourth aspect of the invention is an eddy-current flaw detection device for performing eddy-current flaw detection of a conductive pipe, and comprising: a magnetic element group of which a specified number of magnetic elements are evenly spaced in each of at least two rows that are formed around the surface of a column shaped casing that is formed such that it can be inserted into the conductive pipe, with one of the two rows being located at a position that differs from the other row by ½ the even spacing in the row direction; and switching circuits for switching the magnetic elements in the respective row of the magnetic element group at time-division, and is characterized by comprising: magnetic field excitation means for causing the magnetic elements in one row to function as magnetic field excitation elements that excite magnetic fields by being switched at time-division by the switching circuit; and magnetic field detection means for causing the magnetic elements in the other row to function as magnetic field detection elements that detect magnetic fields by being switched at time-division by the switching circuit, wherein the eddy-current flaw detection device performs eddy-current flaw detection of the conductive pipe by detecting each magnetic field that is excited by each magnetic field excitation element of the magnetic field excitation means by two magnetic field detection elements of the magnetic field detection means that are each located at positions that differ from that of the magnetic field excitation element by 3/2 the even spacing in the row direction.

In the eddy-current flaw detection method according to the first aspect of the invention and the eddy-current flaw detection device according to the fourth aspect of the invention, a magnetic element group is provided of which a specified number of magnetic elements are evenly spaced in each of at least two rows that are formed around the surface of a column shaped casing that is formed such that it can be inserted into the conductive pipe, with one of the two rows being located at a position that differs from the other row by ½ the even spacing in the row direction, each switching circuit switches the magnetic elements in the respective row at time-division, and eddy-current flaw detection of the conductive pipe is performed. The magnetic elements in one row function as magnetic field excitation elements that excite magnetic fields by being switched at time-division, and magnetic elements in the other row function as magnetic field detection elements that detect magnetic fields by being switched at time-division. Eddy-current flaw detection of a conductive pipe is performed by detecting each magnetic field that is excited by each magnetic field excitation element by two of the magnetic field detection elements that are located at positions that differ from the magnetic field excitation element by 3/2 the even spacing in the row direction.

The eddy-current flaw detection device according to a fifth aspect of the invention is an eddy-current flaw detection device for performing eddy-current flaw detection of a conductive pipe, and comprising: a magnetic element group of which a specified number of magnetic elements are evenly spaced in each of at least two rows that are formed around the surface of a column shaped casing that is formed such that it can be inserted into the conductive pipe, with one of the two rows being located at a position that differs from the other row by ½ the even spacing in the row direction; and switching circuits for switching the magnetic elements in the respective row of the magnetic element group at time-division, and is characterized in that the magnetic elements in one row are magnetic field excitation elements that excite magnetic fields, the magnetic elements in the other row are magnetic field detection elements that detect magnetic fields, and eddy-current flaw detection of the conductive pipe is performed by detecting each magnetic field that is excited by each magnetic field excitation element being switched at time-division by the switching circuit by two magnetic field detection elements that are each located in the other row at positions that differ from the magnetic field excitation element by 3/2 the even spacing in the row direction.

In the eddy-current flaw detection method according to the second aspect of the invention and the eddy-current flaw detection device according to the fifth aspect of the invention, a magnetic element group is provided of which a specified number of magnetic elements are evenly spaced in each of at least two rows that are formed around the surface of a column shaped casing that is formed such that it can be inserted into the conductive pipe, with one of the two rows being located at a position that differs from the other row by ½ the even spacing in the row direction, each switching circuit switches the magnetic elements in the respective row at time-division, and eddy-current flaw detection of the conductive pipe is performed. The magnetic elements in one row are magnetic field excitation elements that excite a magnetic field, and the magnetic elements in the other row are magnetic detection elements that detect a magnetic field. Eddy-current flaw detection of the conductive pipe is performed by detecting each magnetic fields that are excited by each magnetic field excitation elements that are switched at time-division by two magnetic field detection elements that are each located in the other row at positions that differ from the magnetic field excitation element by 3/2 the even spacing in the row direction and that are switched at time-division.

The eddy-current flaw detection device according to a sixth aspect of the invention is an eddy-current flaw detection device comprising a magnetic element group of which a specified number of magnetic elements are evenly spaced in each of at least two rows, with one of the two rows being located at a position that differs from the other row by ½ the even spacing in the row direction, and switching circuits for switching the magnetic elements in the respective row of the magnetic element group at time-division; and is characterized by comprising: magnetic field excitation means for causing the magnetic elements in one row to function as magnetic field excitation elements that excite magnetic fields by being switched at time-division by the switching circuit, and magnetic field detection means for causing the magnetic elements in the other row to function as magnetic field detection elements that detect magnetic fields by being switched at time-division by the switching circuit, wherein the eddy-current flaw detection device performs eddy-current flaw detection by detecting each magnetic field that is excited by each magnetic field excitation element of the magnetic field excitation means by one or two magnetic field detection elements of the magnetic field detection means that are each located at positions that differ from that of the magnetic field excitation element by 3/2 the even spacing in the row direction.

In the eddy-current flaw detection device according to the sixth aspect of the invention, a magnetic element group is provided of which a specified number of magnetic elements are evenly spaced in each of at least two rows, with one of the two rows being located at a position that differs from the other row by ½ the even spacing in the row direction, and each switching circuit switches the magnetic elements of each row at time-division. The magnetic elements in one row function as magnetic field excitation elements that excite a magnetic field by being switched at time-division, and the magnetic elements in the other row function as magnetic detection elements that detect a magnetic field by being switched at time-division. Eddy-current flaw detection is performed by detecting each magnetic field that is excited by each magnetic field excitation element by one or two magnetic field detection elements that are each located at positions that differ from the magnetic field excitation element by 3/2 the even spacing in the row direction.

The eddy-current flaw detection device according to a seventh aspect of the invention is an eddy-current flaw detection device comprising: a magnetic element group of which a specified number of magnetic elements are evenly spaced in each of at least two rows, with one of the two rows being located at a position that differs from the other row by ½ the even spacing in the row direction; and switching circuits for switching the magnetic elements in the respective row of the magnetic element group at time-division, and is characterized in that the magnetic elements in one row are magnetic field excitation elements that excite a magnetic field, the magnetic elements in the other row are magnetic field detection elements that detect a magnetic field, and eddy-current flaw detection is performed by detecting each magnetic field that is excited by each magnetic field excitation element that is switched at time-division by the switching circuit by one or two magnetic field detection elements that are each located in the other row at positions that differ from the magnetic field excitation element by 3/2 the even spacing in the row direction and that are switched at time-division by the switching circuit.

In the eddy-current flaw detection device according to the seventh aspect of the invention, a magnetic element group is provided of which a specified number of magnetic elements are evenly spaced in each of at least two rows, with one of the two rows being located at a position that differs from the other row by ½ the even spacing in the row direction, and each switching circuit switches the magnetic elements in the respective row at time-division. The magnetic elements in one row are magnetic field excitation elements that excite a magnetic field, and the magnetic elements in the other row are magnetic field detection elements that detect a magnetic field. Eddy-current flaw detection is performed by detecting each magnetic field that is excited by each magnetic field excitation element that is switched at time-division by one or two magnetic field detection elements that are each located in the other row at positions that differ from that of the magnetic field excitation element by 3/2 the even spacing in the row direction and that are switched at time-division.

The eddy-current flaw detection device according to an eighth aspect of the invention is characterized by further comprising a magnetic element group that is located in a row around the surface of the casing adjacent to the other row, and a switching circuit for switching the magnetic element group at time-division, and performing eddy-current flaw detection by detecting an excited magnetic field by two magnetic elements that are located in the row and that are switched by the switching circuit.

In the eddy-current flaw detection method according to the third aspect of the invention and the eddy-current flaw detection device according to the eighth aspect of the invention, another magnetic element group is additionally located in a row around the surface of the casing adjacent to the other row, and that additionally provided magnetic element group is switched at time-division by an additionally provided switching circuit. Eddy-current flaw detection is performed by detecting an excited magnetic field by two magnetic elements that are located in the additional row and that are switched at time-division by the switching circuit.

The eddy-current flaw detection device according to a ninth aspect of the invention is characterized by further comprising an amplifier circuit for amplifying a signal that each of the magnetic field detection elements outputted via the switching circuit.

The eddy-current flaw detection probe according to a tenth aspect of the invention is an eddy-current flaw detection probe for performing eddy-current flaw detection of a conductive pipe, and comprising: a magnetic element group of which a specified number of elements are evenly spaced in each of at least two rows that are formed around the surface of a column shaped casing that is formed such that it can be inserted into the conductive pipe, with one of the two rows being located at a position that differs from that of the other row by ½ the even spacing in the row direction; and switching circuits for switching the magnetic elements in the respective row of the magnetic element group at time-division, and is characterized in that the magnetic elements in one row are constructed as magnetic field excitation elements that excite a magnetic field by being switched at time-division by the switching circuit, the magnetic elements in the other row are constructed as magnetic field detection elements that detect a magnetic field by being switched at time-division by the switching circuit, and eddy-current flaw detection of the conductive pipe is performed by detecting each magnetic field that is excited by each magnetic element that functions as the magnetic field excitation element by two the magnetic elements that function as the magnetic field detection elements and that are located at positions that differ from that of the magnetic field excitation element by 3/2 the even spacing in the row direction.

In the eddy-current flaw detection probe according to the tenth aspect of the invention, a magnetic element group is provided of which a specified number of elements are evenly spaced in each of at least two rows that are formed around the surface of a column shaped casing that is formed such that it can be inserted into a conductive pipe, with one of the two rows being located at a position that differs from that of the other row by ½ the even spacing in the row direction. Eddy-current flaw detection is performed by causing the switching circuits to switch the magnetic elements in the respective row at time-division. The magnetic elements in one row function as magnetic field excitation elements that excite a magnetic field by being switched at time-division, and the magnetic elements in the other row function as magnetic field detection elements that detect a magnetic field by being switched at time-division. Eddy-current flaw detection of a conductive pipe is performed by detecting each magnetic field that is excited by each magnetic element that functions as the magnetic field excitation element by two of the magnetic elements that function as magnetic field detection elements and that are located at positions that differ from that of the magnetic field excitation element by 3/2 the even spacing in the row direction.

The eddy-current flaw detection probe according to an eleventh aspect of the invention is an eddy-current flaw detection probe for performing eddy-current flaw detection of a conductive pipe, and comprising: a magnetic element group of which a specified number of elements are evenly spaced in each of at least two rows that are formed around the surface of a column shaped casing that is formed such that it can be inserted into the conductive pipe, with one of the two rows being located at a position that differs from that of the other row by ½ the even spacing in the row direction; and switching circuits for switching the magnetic elements in the respective row of the magnetic element group at time-division, and is characterized in that the magnetic elements in one row are magnetic field excitation elements that excite a magnetic field, the magnetic elements in the other row are magnetic field detection elements that detect a magnetic field, and eddy-current flaw detection of the conductive pipe is performed by detecting each magnetic field that is excited by each magnetic field excitation element that is switched at time-division by the switching circuit by two magnetic field detection elements that are each located in the other row at positions that differ from the magnetic field excitation element by 3/2 the even spacing in the row direction and that are switched at time-division by the switching circuit.

In the eddy-current flaw detection probe according to the eleventh aspect of the invention, a magnetic element group is provided of which a specified number of magnetic elements are evenly spaced in each of at least two rows that are formed around the surface of a column shaped casing that is formed such that it can be inserted into a conductive pipe, with one of the two rows being located at a position that differs from that of the other row by ½ the even spacing in the row direction. Eddy-current flaw detection is performed by causing the switching circuits to switch the magnetic elements in the respective row at time-division. The magnetic elements in one row are magnetic field excitation elements that excite a magnetic field, and the magnetic elements in the other row are magnetic field detection elements that detect a magnetic field. Eddy-current flaw detection of the conductive pipe is performed by detecting each magnetic field that is excited by each magnetic field excitation element that is switched at time-division by two magnetic field detection elements that are each located in the other row at positions that differ from that of the magnetic field excitation element by 3/2 the even spacing in the row direction and that are switched at time-division.

The eddy-current flaw detection probe according to a twelfth aspect of the invention is an eddy-current flaw detection probe that comprises: a magnetic element group of which a specified number of elements are evenly spaced in each of at least two rows, with one of the two rows being located at a position that differs from that of the other row by ½ the even spacing in the row direction; and switching circuits for switching the magnetic elements in the respective row of the magnetic element group at time-division, and is characterized in that the magnetic elements in one row are constructed as magnetic field excitation elements that excite a magnetic field by being switched at time-division by the switching circuit, the magnetic elements in the other row are constructed as magnetic field detection elements that detect a magnetic field by being switched at time-division by the switching circuit, and eddy-current flaw detection is performed by detecting each magnetic field that is excited by each magnetic element that functions as a magnetic field excitation element by one or two of the magnetic elements that function as the magnetic field detection elements and that are located at positions that differ from that of the magnetic field excitation element by 3/2 the even spacing in the row direction.

In the eddy-current flaw detection probe according to the twelfth aspect of the invention, a magnetic element group is provided of which a specified number of magnetic elements are evenly spaced in each of at least two rows, with one of the two rows being located at a position that differs from that of the other row by ½ the even spacing in the row direction, and each switching circuit switches the magnetic elements in the respective row at time-division. The magnetic elements in one row function as magnetic field excitation elements that excite a magnetic field by being switched at time-division, and the magnetic elements in the other row function as magnetic field detection elements that detect a magnetic field by being switched at time-division. Eddy-current flaw detection is performed by detecting each magnetic field that is excited by each magnetic element that functions as the magnetic field excitation element by one or two of the magnetic elements that function as the magnetic field detection elements and that are located at positions that differ from that of the magnetic field excitation element by 3/2 the even spacing in the row direction.

The eddy-current flaw detection probe according to a thirteenth aspect of the invention is an eddy-current flaw detection probe that comprises: a magnetic element group of which a specified number of elements are evenly spaced in each of at least two rows, with one of the two rows being located at a position that differs from that of the other row by ½ the even spacing in the row direction; and switching circuits for switching the magnetic elements in the respective row of the magnetic element group at time-division, and is characterized in that the magnetic elements in one row are magnetic field excitation elements that excite a magnetic field, the magnetic elements in the other row are magnetic field detection elements that detect a magnetic field, and eddy-current flaw detection is performed by detecting each magnetic field that is excited by each magnetic field excitation element that is switched at time-division by the switching circuit by one or two magnetic field detection elements that are each located in the other row at positions that differ from the magnetic field excitation element by 3/2 the even spacing in the row direction and that are switched at time-division by the switching circuit.

In the eddy-current flaw detection probe according to the thirteenth aspect of the invention, a magnetic element group is provided of which a specified number of magnetic elements are evenly spaced in each of at least two rows, with one of the two rows being located at a position that differs from that of the other row by ½ the even spacing in the row direction, each switching circuit switches the magnetic elements in the respective row at time-division. The magnetic elements in one row are magnetic field excitation elements that excite a magnetic field, and the magnetic elements in the other row are magnetic field detection elements that detect a magnetic field. Eddy-current flaw detection is performed by detecting each magnetic field that is excited by each magnetic field excitation element that is switched at time-division by one or two magnetic field detection elements that are each located in the other row at positions that differ from that of the magnetic field excitation element by 3/2 the even spacing in the row direction and that are switched at time-division.

The eddy-current flaw detection probe according to a fourteenth aspect of the invention is characterized by further comprising: a magnetic element group that is located in a row around the surface of the casing adjacent to the other row; and a switching circuit for switching the magnetic element group at time-division, and performing eddy-current flaw detection by detecting the excited magnetic field by two magnetic elements that are located in the row and that are switched at time-division.

In the eddy-current flaw detection probe according to the fourteenth aspect of the invention, a magnetic element group is additionally provided in a row around the surface of the casing adjacent to the other row, and an additionally provided switching circuit switches the additionally provided magnetic element group at time-division. Eddy-current flaw detection is performed by detecting the excited magnetic field by switching two magnetic elements of that magnetic element group at time-division.

The eddy-current flaw detection probe according to a fifteenth aspect of the invention is characterized by further comprising an amplifier circuit for amplifying a signal that each of the magnetic field detection elements outputted via a switching circuit.

With the eddy-current flaw detection method according to the first to third aspects of the invention, it is possible to provide an eddy-current flaw detection method that improves the spatial resolution of flaw detection signals as well as signal reproducibility during redetection of flaws, and reduces signal interference due to crosstalk with a simple circuit construction.

With the eddy-current flaw detection device according to the fourth to ninth aspects of the invention, it is possible to provide an eddy-current flaw detection device that improves the spatial resolution of flaw detection signals as well as signal reproducibility during redetection of flaws, and reduces signal interference due to crosstalk with a simple circuit construction.

With the eddy-current flaw detection probe according to the tenth to fifteenth aspects of the invention, it is possible to provide an eddy-current flaw detection probe that improves the spatial resolution of flaw detection signals as well as signal reproducibility during redetection of flaws, and reduces signal interference due to crosstalk with a simple circuit construction.

The above and further objects and features will more fully be apparent from the following detailed description with accompanying drawings.

DETAILED DESCRIPTION

The following description will explain the present invention in detail on the basis of the drawings illustrating some embodiments thereof.

Figure 4:
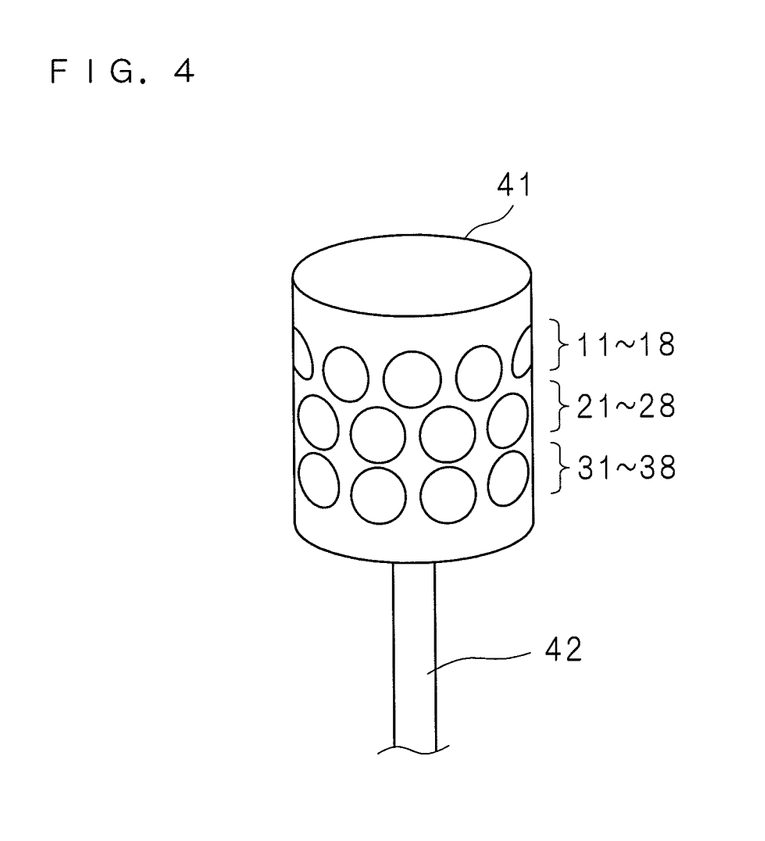
FIG. 4 is a perspective drawing schematically illustrating the external appearance of an eddy-current flaw detection probe that is used in an embodiment of a eddy-current flaw detection method, eddy-current flaw detection device and eddy-current flaw detection probe of the present invention.

FIG. 4 is a perspective drawing schematically illustrating the external appearance of an eddy-current flaw detection probe that is used in an embodiment of the eddy-current flaw detection method, eddy-current flaw detection device and eddy-current flaw detection probe of the present invention.

This eddy-current flaw detection probe comprises a column shaped casing (housing) 41 that is formed such that it can be gently inserted inside a slim metal pipe, and eight coils 11 to 18, 21 to 28, 31 to 38, that are aligned around the outer surface of the casing 41, are evenly spaced in each of three rows. The coils 11 to 18 of the first row of the three rows are arranged such that they are located at a position in the circumferential direction that differs from that of the coils 21 to 28 and 31 to 38 of the other two rows by ½ the equal spacing.

Figure 5:
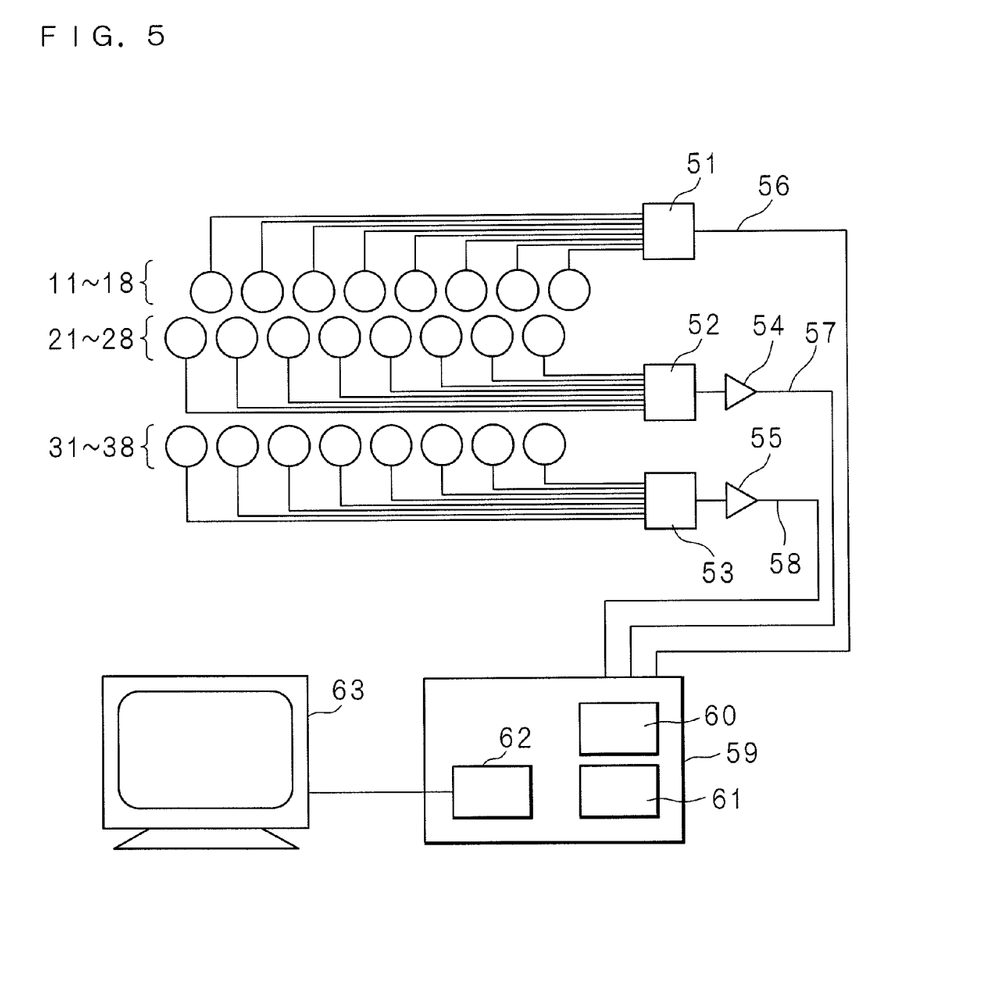
FIG. 5 is a block diagram illustrating circuit construction inside the casing of an eddy-current flaw detection probe and eddy-current flaw detection device of the present invention.

FIG. 5 is a block diagram illustrating the circuit construction inside the casing 41 and eddy-current flaw detection device.

The coils (magnetic elements, magnetic field excitation means) 11 to 18 in the first row are coils that are used as magnetic field excitation coils (magnetic field excitation elements) that generate an eddy current in the thickness section from the inner surface of a slim metal pipe, and each is connected to a multiplexer (switching circuit) 51 for magnetic field excitation.

A lead wire 56 is connected to the multiplexer 51 for magnetic field excitation, and an AC current for exciting a magnetic field is applied to the lead wire 56 from the main unit 59 of the eddy-current flaw detection device.

Moreover, the coils (magnetic elements, magnetic field detection means) 21 to 28 in the second row are coils that are used as magnetic field detection coils (magnetic field detection elements) that detect a magnetic field according to an eddy current that is generated in the thickness section of a slim metal pipe, and each is connected to a multiplexer (switching circuit) 52 for magnetic field detection. An amplifier (magnetic field detection means) 54, which amplifies the output signals of the magnetic field that is detected by the coils 21 to 28, is connected to the multiplexer 52 for magnetic field detection, and the amplified signal from the amplifier 54 is outputted to the main unit 59 of the eddy-current flaw detection device via a lead wire 57.

The coils (magnetic elements, magnetic field detection means) 31 to 38 in the third row are coils used for magnetic field detection, and each is connected to a multiplexer (switching circuit) 53 for magnetic field detection. An amplifier (magnetic field detection means) 55, which amplifies the output signal of the magnetic field that is detected by the coils 31 to 38, is connected to the multiplexer 53 for magnetic field detection, and the amplified signal from the amplifier 55 is outputted to the main unit 59 of the eddy-current flaw detection device via a lead wire 58.

As shown in FIG. 4, the lead wires 56 to 58 are stored inside a cable 42 that connects the center section of the surface on one end of the casing 41 of the eddy-current flaw detection probe with the main unit 59 of the eddy-current flaw detection device.

An oscillation circuit (magnetic field excitation means) 60 that generates an AC current for exciting a magnetic field by the coils 11 to 18, a signal detection circuit 61 that obtains amplified detection signals of magnetic fields they are detected by coils 21 to 28 and 31 to 38, and a communication unit 62 for communicating with a personal computer (or workstation) 63 are located inside of the main unit 59 of the eddy-current flaw detection device. The personal computer 63 receives the detection signal that was obtained by the signal detection circuit 61 via the communication unit 62 as detection data, and records and displays the received detection data.

The amplifiers 54 and 55 can also be located inside of the main unit 59 of the eddy-current flaw detection device, and when a small number of coils are in each row, the multiplexers 51 to 53 could also be located inside of the main unit 59 of the eddy-current flaw detection device.

FIGS. 6A to 6D are expanded views explaining the operation of an eddy-current flaw detection probe having this kind of construction, and illustrating a planar expansion of the coils 11 to 18, 21 to 28 and 31 to 38 shown in FIG. 4.

This eddy-current flaw detection probe detects flaws for the amount of one circumference of the inner surface of a slim metal pipe in first through eighth timeslots indicating the cycle of the operation.

According to the eddy-current flaw detection probe, in the first timeslot (FIG. 6A), the multiplexer 51 selects coil 11 as the magnetic field excitation coil T, and the multiplexer 52 selects coils 28 and 23 in the second row, which are separated from the coil 11 by the amount of 3/2 coils in the circumferential direction, as magnetic field detection coils R1 and R2. In addition, the multiplexer 53 selects coils 31 and 32 in the third row, which are separated from coil 11 by the amount of 0.5 coil in the circumferential direction, as magnetic field detection coils R3 and R4.

Figure 6A:
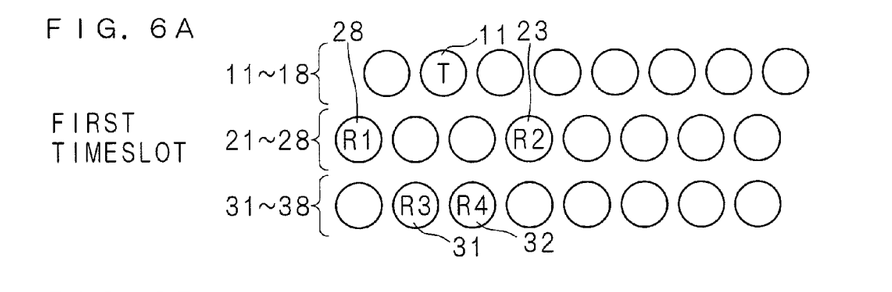
FIG. 6A is an expanded view explaining the operation of the eddy-current flaw detection method, eddy-current flaw detection device and eddy-current flaw detection probe of the present invention during a first timeslot, and illustrating a planar expansion of the coils shown in FIG. 4.
Figure 6B:
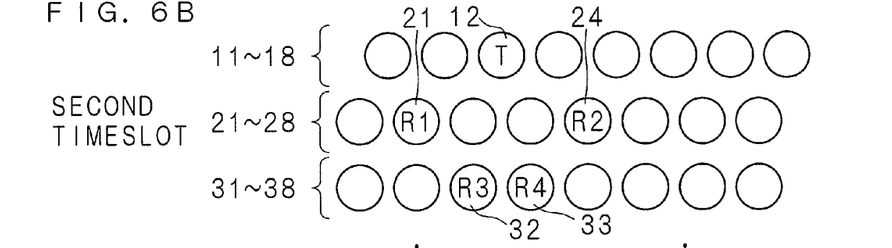
FIG. 6B is an expanded view explaining the operation of the eddy-current flaw detection method, eddy-current flaw detection device and eddy-current flaw detection probe of the present invention during a second timeslot, and illustrating a planar expansion of the coils shown in FIG. 4.
Figure 6C:
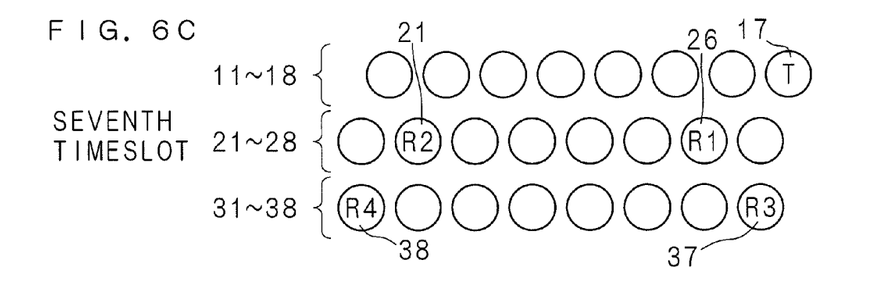
FIG. 6C is an expanded view explaining the operation of the eddy-current flaw detection method, eddy-current flaw detection device and eddy-current flaw detection probe of the present invention during a seventh timeslot, and illustrating a planar expansion of the coils shown in FIG. 4.
Figure 6D:
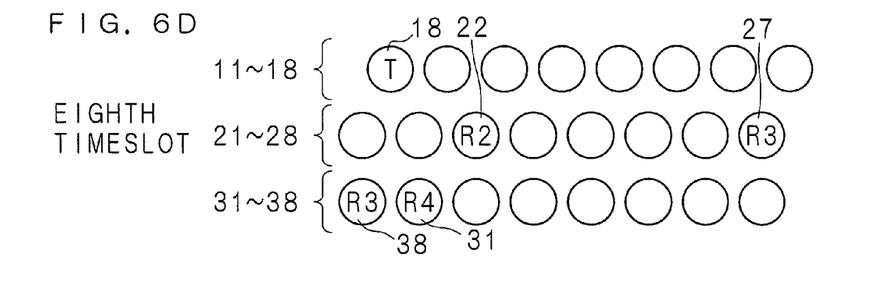
FIG. 6D is an expanded view explaining the operation of the eddy-current flaw detection method, eddy-current flaw detection device and eddy-current flaw detection probe of the present invention during an eighth timeslot, and illustrating a planar expansion of the coils shown in FIG. 4.

The detection signals that are outputted by the magnetic field detection coils R1, R2 are used for detecting flaws in the circumferential direction of the slim metal pipe (direction that orthogonally crosses the advancement direction of the eddy-current flaw detection probe), and the detection signals that are outputted by the magnetic field detection coils R3, R4 are used for detecting flaws in the axial direction of the slim metal pipe (advancement direction of the eddy-current flaw detection probe).

According to the eddy-current flaw detection probe, in the second timeslot (FIG. 6B), the multiplexer 51 selects coil 12 as the magnetic field excitation coil T, and the multiplexer 52 selects coils 21 and 24 in the second row, which are separated from the coil 12 by the amount of 3/2 coils in the circumferential direction, as magnetic field detection coils R1 and R2. In addition, the multiplexer 53 selects coils 32 and 33 in the third row, which are separated from coil 12 by the amount of 0.5 coil in the circumferential direction, as magnetic field detection coils R3 and R4.

In each timeslot after that, the multiplexer 51 sequentially selects coils 13, 14, 15, . . . as the magnetic field excitation coil T, and the multiplexer 52 sequentially selects pairs of coils 22•25, 23•26, 24•27, . . . as the magnetic field detection coils R1•R2. In addition, the multiplexer 53 sequentially selects pairs of coils 33•34, 34•35, 35•36, . . . as the magnetic field detection coils R3•R4.

According to the eddy-current flaw detection probe, in the seventh timeslot (FIG. 6C), the multiplexer 51 selects coil 17 as the magnetic field excitation coil T, and the multiplexer 52 selects coils 26 and 21 in the second row, which are separated from the coil 17 by the amount of 3/2 coils in the circumferential direction, as magnetic field detection coils R1 and R2. In addition, the multiplexer 53 selects coils 37 and 38 in the third row, which are separated from coil 17 by the amount of 0.5 coil in the circumferential direction, as magnetic field detection coils R3 and R4.

According to the eddy-current flaw detection probe, in the eighth timeslot (FIG. 6D), the multiplexer 51 selects coil 18 as the magnetic field excitation coil T, and the multiplexer 52 selects coils 27 and 22 in the second row, which are separated from the coil 18 by the amount of 3/2 coils in the circumferential direction, as magnetic field detection coils R1 and R2. In addition, the multiplexer 53 selects coils 38 and 31 in the third row, which are separated from coil 18 by the amount of 0.5 coil in the circumferential direction, as magnetic field detection coils R3 and R4.

Depending on the first through eighth timeslots described above, the combinations of the magnetic field excitation coil T and magnetic field detection coil R1, and the magnetic field excitation coil T and magnetic field detection coil R2 are suitably located for detecting flaws in the circumferential direction of the slim metal pipe (direction that orthogonally crosses the advancement direction of the eddy-current flaw detection probe). Also, the combinations of the magnetic field excitation coil T and the magnetic field detection coil R3, and the magnetic field excitation coil T and the magnetic field detection coil R4 are suitably located for detecting flaws in the axial direction of the slim metal pipe (advancement direction of the eddy-current flaw detection probe).

In the case of this embodiment, since output of the 16 channels by the coils 21 to 28 is obtained for the same circumference per one circumference of the slim metal pipe, there is no need for compensating for shifting in the axial direction, and thus the spatial resolution of flaw detection signals, and the reproducibility during redetection of flaws are improved.

Moreover, as shown in FIG. 5, when compared with the conventional circuit shown in FIG. 2, there is no need for two multiplexers, as well as there is no need for wiring from coils 11 to 18 of the first row and coils 21 to 28 of the second row to each of the two multiplexers, so the circuit construction can be made more compact, and the entire circuit can be stored inside the casing 41 of the eddy-current flaw detection probe. In addition, by reducing the amount of wiring, interference signals due to crosstalk can be reduced.

Depending on the performance and the like of the eddy-current flaw detection device, it is possible to combine two timeslots. For example, in the first timeslot, it is possible to simultaneously select coils 11 and 15 as magnetic field excitation coils, and to simultaneously select coils 31, 32, 28, 23, 35, 36, 24 and 27 as magnetic field detection coils.

An amplifier circuit is normally necessary in order to amplify detection signals from the multiplexer, however, in cases where the deterioration of the detection signals is not especially a problem, it is also possible to omit the amplifier circuit.

Moreover, this embodiment illustrates an example of an insert type probe that is inserted inside a slim metal pipe, however, the present invention can also be applied to a top placement type or penetrating type eddy-current flaw detection device and eddy-current flaw detection probe.

Furthermore, in this embodiment, coils were used as both magnetic field excitation elements and magnetic field detection elements, however, the invention is not limited to this, and of course it is possible to use other elements. Also, a clear distinction is made between magnetic field excitation element groups and magnetic field detection element groups, so, for example, it is possible to combine different kinds of elements such using a coil as a magnetic field excitation element and using a magnetic detection element such as a hole element, magnetic resistance effect element and the like as a magnetic field detection element.

Moreover, the direction of the coils is not limited to that shown in FIG. 4, and construction using other directions is possible.

Furthermore, the number of coils is not necessarily limited to eight coils per row, and can be suitably increased or decreased as needed. In addition, similarly the number of channels of the multiplexer, which is a switching circuit, can be suitably increased or decreased as needed. Also, the most preferable location for the circuit to be located is inside the casing of the eddy-current flaw detection probe, however, in the case where that is physically impossible, the circuit can be provided inside of or around the pipe that stores the wiring.

The present invention can be applied to an eddy-current flaw detection method, eddy-current flaw detection device and eddy-current flaw detection probe that are used in non-destructive inspection (eddy-current flaw detection testing) of a heat transfer pipe inside of a heat exchanger.

As this description may be embodied in several forms without departing from the spirit of essential characteristics thereof, the present embodiments are therefore illustrative and not restrictive, since the scope is defined by the appended claims rather than by the description preceding them, and all changes that fall within metes and bounds of the claims, or equivalence of such metes and bounds thereof are therefore intended to be embraced by the claims.

What is claimed is:

1. An eddy-current flaw detection method for performing eddy-current flaw detection of a conductive pipe by using a magnetic element group of which a specified number of magnetic elements, which excite or detect a magnetic field, are evenly spaced in each of at least two rows that are formed around the surface of a column shaped casing that is formed such that it can be inserted into the conductive pipe, with one of the two rows being located at a position that differs from the other row by ½ the even spacing in the row direction, and switching circuits for switching the magnetic elements in the respective row of the magnetic element group at time-division, comprising:
   a step of causing the switching circuit to switch the magnetic elements in one row at time-division in order to excite a magnetic field; and
   a step of causing the switching circuit to switch, at time-division, two magnetic elements that are arranged in the other row and that are located at positions that differ from the magnetic element that excited the magnetic field by 3/2 the even spacing in the row direction in order to detect the excited magnetic field.

2. An eddy-current flaw detection method for performing eddy-current flaw detection of a conductive pipe by using a magnetic element group of which a specified number of magnetic elements, which excite or detect a magnetic field, are evenly spaced in each of at least two rows that are formed around the surface of a column shaped casing that is formed such that it can be inserted into the conductive pipe, with one of the two rows being located at a position that differs from the other row by ½ the even spacing in the row direction, and switching circuits for switching the magnetic elements in the respective row of the magnetic element group at time-division, comprising:
   a step of preparing the magnetic elements in one row as magnetic field excitation elements that excite a magnetic field, and the magnetic elements in the other row as magnetic field detection elements that detect a magnetic field;
   a step of causing the switching circuit to switch the magnetic field excitation elements at time-division in order to excite a magnetic field; and
   a step of causing the switching circuit to switch, at time-division, two magnetic field detection elements that are arranged in the other row and that are located at positions that differ from the magnetic field excitation element which excited the magnetic field by 3/2 the even spacing in the row direction in order to detect the excited magnetic field.

3. The eddy-current flaw detection method according to claim 1, further comprising:
   a step of preparing a magnetic element group being located in a row around the surface of the casing adjacent to the other row, and a switching circuit for switching the magnetic element group at time-division; and
   a step of causing the switching circuit to switch, at time-division, two magnetic elements that are located in the row in order to detect the excited magnetic field.

4. An eddy-current flaw detection device for performing eddy-current flaw detection of a conductive pipe, comprising:
   a magnetic element group of which a specified number of magnetic elements, which excite or detect a magnetic field, are evenly spaced in each of at least two rows that are formed around the surface of a column shaped casing that is formed such that it can be inserted into the conductive pipe, with one of the two rows being located at a position that differs from the other row by ½ the even spacing in the row direction;
   switching circuits for switching the magnetic elements in the respective row of the magnetic element group at time-division;
   a magnetic field excitation section for causing the magnetic elements in one row to function as magnetic field excitation elements that excite a magnetic field by being switched at time-division by the switching circuit; and a magnetic field detection section for causing the magnetic elements in the other row to function as magnetic field detection elements that detect a magnetic field by being switched at time-division by the switching circuit, wherein the eddy-current flaw detection device performs eddy-current flaw detection of the conductive pipe by detecting each magnetic field that is excited by each magnetic field excitation element by two magnetic field detection elements that are each located at positions that differ from the magnetic field excitation element by 3/2 the even spacing in the row direction.

5. An eddy-current flaw detection device for performing eddy-current flaw detection of a conductive pipe, comprising:

a magnetic element group of which a specified number of magnetic elements, which excite or detect a magnetic field, are evenly spaced in each of at least two rows that are formed around the surface of a column shaped casing that is formed such that it can be inserted into the conductive pipe, with one of the two rows being located at a position that differs from the other row by ½ the even spacing in the row direction; and switching circuits for switching the magnetic elements in the respective row of the magnetic element group at time-division, wherein the magnetic elements in one row are magnetic field excitation elements that excite a magnetic field, wherein the magnetic elements in the other row are magnetic field detection elements that detect a magnetic field, and wherein the eddy-current flaw detection device performs eddy-current flaw detection of the conductive pipe by detecting each magnetic field that is excited by each magnetic field excitation element that is switched at time-division by the switching circuit by two magnetic field detection elements that are each located in the other row at positions that differ from the magnetic field excitation element by 3/2 the even spacing in the row direction and that are switched at time-division by the switching circuit.

6. An eddy-current flaw detection device comprising:

a magnetic element group of which a specified number of magnetic elements, which excite or detect a magnetic field, are evenly spaced in each of at least two rows, with one of the two rows being located at a position that differs from the other row by ½the even spacing in the row direction;

switching circuits for switching the magnetic elements in the respective row of the magnetic element group at time-division;

a magnetic field excitation section for causing the magnetic elements in one row to function as magnetic field excitation elements that excite a magnetic field by being switched at time-division by the switching circuit; and a magnetic field detection section for causing the magnetic elements in the other row to function as magnetic field detection elements that detect a magnetic field by being switched at time-division by the switching circuit, wherein the eddy-current flaw detection device performs eddy-current flaw detection by detecting each magnetic field that is excited by each magnetic field excitation element by one or two of the magnetic field detection elements that are each located at positions that differ from the magnetic field excitation element by 3/2 the even spacing in the row direction.

7. An eddy-current flaw detection device comprising a magnetic element group of which a specified number of magnetic elements, which excite or detect a magnetic field, are evenly spaced in each of at least two rows, with one of the two rows being located at a position that differs from the other row by ½ the even spacing in the row direction; and switching circuits for switching the magnetic elements in the respective row of the magnetic element group at time-division, wherein the magnetic elements in one row are magnetic field excitation elements that excite a magnetic field, wherein the magnetic elements in the other row are magnetic field detection elements that detect a magnetic field, and wherein the eddy-current flaw detection device performs eddy-current flaw detection by detecting each magnetic field that is excited by each magnetic field excitation element that is switched at time-division by the switching circuit by one or two of the magnetic field detection elements that are each located in the other row at positions that differ from the magnetic field excitation element by 3/2 the even spacing in the row direction and that are switched at time-division by the switching circuit.

8. The eddy-current flaw detection device according to claim 4, further comprising:

a magnetic element group being located in a row around the surface of the casing adjacent to the other row; and a switching circuit for switching the magnetic element group at time-division, wherein the eddy-current flaw detection device performs eddy-current flaw detection by detecting the excited magnetic field by two magnetic elements that are located in the row and that are switched at time-division by the switching circuit.

9. The eddy-current flaw detection device according to claim 4, further comprising an amplifier circuit for amplifying a signal that each of the magnetic field detection elements outputted via the switching circuit.

10. An eddy-current flaw detection probe for performing eddy-current flaw detection of a conductive pipe, comprising:

a magnetic element group of which a specified number of magnetic elements, which excite or detect a magnetic field, are evenly spaced in each of at least two rows that are formed around the surface of a column shaped casing that is formed such that it can be inserted into the conductive pipe, with one of the two rows being located at a position that differs from the other row by ½ the even spacing in the row direction; and switching circuits for switching the magnetic elements in the respective row of the magnetic element group at time-division, wherein the magnetic elements in one row are constructed as magnetic field excitation elements that excite a magnetic field by being switched at time-division by the switching circuit, wherein the magnetic elements in the other row are constructed as magnetic field detection elements that detect a magnetic field by being switched at time-division by the switching circuit, and wherein the eddy-current flaw detection probe performs eddy-current flaw detection of the conductive pipe by detecting each magnetic field that is excited by each magnetic element that functions as the magnetic field excitation element by two magnetic elements that function as the magnetic field detection elements and that are located at positions that differ from the magnetic field excitation element by 3/2 the even spacing in the row direction.

11. An eddy-current flaw detection probe for performing eddy-current flaw detection of a conductive pipe, comprising:
a magnetic element group of which a specified number of magnetic elements, which excite or detect a magnetic field, are evenly spaced in each of at least two rows that are formed around the surface of a column shaped casing that is formed such that it can be inserted into the conductive pipe, with one of the two rows being located at a position that differs from the other row by ½ the even spacing in the row direction; and
switching circuits for switching the magnetic elements in the respective row of the magnetic element group at time-division,
wherein the magnetic elements in one row are magnetic field excitation elements that excite a magnetic field,
wherein the magnetic elements in the other row are magnetic field detection elements that detect a magnetic field, and
wherein the eddy-current flaw detection probe performs eddy-current flaw detection of the conductive pipe by detecting each magnetic field that is excited by each magnetic field excitation element that is switched at time-division by the switching circuit by two magnetic field detection elements that are each located in the other row at positions that differ from the magnetic field excitation element by 3/2 the even spacing in the row direction and that are switched at time-division by the switching circuit.

12. An eddy-current flaw detection probe comprising a magnetic element group of which a specified number of magnetic elements, which excite or detect a magnetic field, are evenly spaced in each of at least two rows, with one of the two rows being located at a position that differs from the other row by ½ the even spacing in the row direction; and
switching circuits for switching the magnetic elements in the respective row of the magnetic element group at time-division,
wherein the magnetic elements in one row are constructed as magnetic field excitation elements that excite a magnetic field by being switched at time-division by the switching circuit,
wherein the magnetic elements in the other row are constructed as magnetic field detection elements that detect a magnetic field by being switched at time-division by the switching circuit, and
wherein the eddy-current flaw detection probe performs eddy-current flaw detection by detecting each magnetic field that is excited by each magnetic element that functions as the magnetic field excitation element by one or two of the magnetic elements that function as the magnetic field detection elements and that are located at positions that differ from the magnetic field excitation element by 3/2 the even spacing in the row direction.

13. An eddy-current flaw detection probe comprising:
a magnetic element group of which a specified number of magnetic elements, which excite or detect a magnetic field, are evenly spaced in each of at least two rows, with one of the two rows being located at a position that differs from the other row by ½ the even spacing in the row direction; and
switching circuits for switching the magnetic elements in the respective row of the magnetic element group at time-division,
wherein the magnetic elements in one row are magnetic field excitation elements that excite a magnetic field,
wherein the magnetic elements in the other row are magnetic field detection elements that detect a magnetic field, and
wherein the eddy-current flaw detection probe performs eddy-current flaw detection by detecting each magnetic field that is excited by each magnetic field excitation element that is switched at time-division by the switching circuit by one or two of the magnetic field detection elements that are each located in the other row at positions that differ from the magnetic field excitation element by 3/2 the even spacing in the row direction and that are switched at time-division by the switching circuit.

14. The eddy-current flaw detection probe according to claim 10, further comprising:
a magnetic element group being located in a row around the surface of the casing adjacent to the other row; and
a switching circuit for switching the magnetic element group at time-division,
wherein the eddy-current flaw detection probe performs eddy-current flaw detection by detecting the excited magnetic field by two magnetic elements that are located in the row and that are switched at time-division by the switching circuit.

15. The eddy-current flaw detection probe according to claim 10, further comprising an amplifier circuit for amplifying a signal that each of the magnetic field detection elements outputted via the switching circuit.

16. The eddy-current flaw detection method according to claim 2, further comprising:
a step of preparing a magnetic element group being located in a row around the surface of the casing adjacent to the other row, and a switching circuit for switching the magnetic element group at time-division; and
a step of causing the switching circuit to switch, at time-division, two magnetic elements that are located in the row in order to detect the excited magnetic field.

17. The eddy-current flaw detection device according to claim 5, further comprising:
a magnetic element group being located in a row around the surface of the casing adjacent to the other row; and
a switching circuit for switching the magnetic element group at time-division, wherein
the eddy-current flaw detection device performs eddy-current flaw detection by detecting the excited magnetic field by two magnetic elements that are located in the row and that are switched at time-division by the switching circuit.

18. The eddy-current flaw detection device according to claim 5, further comprising an amplifier circuit for amplifying a signal that each of the magnetic field detection elements outputted via the switching circuit.

19. The eddy-current flaw detection probe according to claim 11, further comprising:
a magnetic element group being located in a row around the surface of the casing adjacent to the other row; and
a switching circuit for switching the magnetic element group at time-division,
wherein the eddy-current flaw detection probe performs eddy-current flaw detection by detecting the excited magnetic field by two magnetic elements that are located in the row and that are switched at time-division by the switching circuit.

20. The eddy-current flaw detection probe according to claim 11, further comprising an amplifier circuit for amplifying a signal that each of the magnetic field detection elements outputted via the switching circuit.

* * * * *